(12) United States Patent
Sumiya

(10) Patent No.: US 7,244,027 B2
(45) Date of Patent: Jul. 17, 2007

(54) PERIMETER

(75) Inventor: Toshifumi Sumiya, Nukata-gun (JP)

(73) Assignee: Nidek Co., Ltd., Aichi (JP)

( * ) Notice: Subject to any disclaimer, the term of this patent is extended or adjusted under 35 U.S.C. 154(b) by 231 days.

(21) Appl. No.: 11/170,791

(22) Filed: Jun. 30, 2005

(65) Prior Publication Data

US 2006/0001831 A1    Jan. 5, 2006

(30) Foreign Application Priority Data

Jun. 30, 2004   (JP)   ............... P2004-195046

(51) Int. Cl.
*A61B 3/10*   (2006.01)
*A61B 3/02*   (2006.01)
(52) U.S. Cl. .............. 351/224; 351/226; 351/211
(58) Field of Classification Search ......... 351/224, 351/226
See application file for complete search history.

(56) References Cited

U.S. PATENT DOCUMENTS 4,832,480 A * 5/1989 Kornacker et al. ......... 351/246
5,323,194 A    6/1994 Campbell et al.
5,598,235 A * 1/1997 Heijl et al. ............... 351/224
6,685,321 B2 * 2/2004 Suzumura et al. ......... 351/224

FOREIGN PATENT DOCUMENTS

JP        06-054804 A    3/1994
JP        7-504589 A     5/1995

OTHER PUBLICATIONS

Obtronics (2002) No. 7, p. 199-204 with partial English translation of (3. Brief Summary of Optical Topography: 3.1 Image Measuring Method of Brain Activity) in pp. 200-201.

* cited by examiner

*Primary Examiner*—Jordan Schwartz
*Assistant Examiner*—James C. Jones
(74) *Attorney, Agent, or Firm*—Sughrue Mion, PLLC

(57) ABSTRACT

A perimeter for examining a visual field condition of an examinee's eye, includes: a target presenting unit a response unit brain activity detecting unit which detects an activity condition of a visual cortex of the examinee; and an operation unit which determines if the response with the response unit with respect to presentation of the target is resulted from a fact that the examinee can perceive the target based on a detection result of the brain activity detecting unit and which obtains the visual field condition on the basis of the presentation condition of the target and the response result in consideration of the determination result of the brain activity detecting unit.

5 Claims, 3 Drawing Sheets

PERIMETER

BACKGROUND OF THE INVENTION

The present invention relates to a perimeter for examining a state of a visual field of an examinee's eye.

When diagnosing disease such as glaucoma, examining (measuring) the state of the visual field (perimetry) is considered to be effective. As an apparatus for examining the state of the visual field (perimeter), such an apparatus is known in which a stimulation target (optotype) for examination is projected on a dome-shaped screen or is displayed on an electronic display unit such as a liquid crystal display to be presented to the examinee's eye fixing to (gazing at) a predetermined fixation point while varying a presentation position and presentation brightness (luminance) of the target, distribution of optical (visual) sensitivity at each examination point an a retina of the examinee's eye corresponding to each presentation position is examined (measured) by obtaining whether or not the examinee can perceive (visually recognize) the presented target. Then, according to this kind of perimeter, the examinee responds by pushing a response button when the examinee perceives the presented target.

However, it depends on the examinee's consciousness whether or not the examinee can perceive the presented target. Therefore, even if the examinee pushes the response button although the examinee cannot perceive the target, it is detected that the examinee could perceive the target, so that the precise examination result cannot be acquired.

SUMMARY OF THE INVENTION

The present invention has been made taking the foregoing problems into consideration and a technical object of which is to provide a perimeter capable of precisely examining a state of a view field without only depending on the examinee's consciousness.

The present invention is characterized by the following constitution sin order to solve the above-described problem.

(1) A perimeter for examining visual field condition of an examinee's eye, the perimeter comprising:
a target presenting unit which presents a stimulation target for examination to the examinee's eye, a presentation condition of the target including a presentation position of the target being variable;
a response unit with which the examinee responds when the examinee can perceive the presented target;
a brain activity detecting unit which detects activity condition of a visual cortex of the examinee; and
an operation unit which determines whether or not the response with the response unit with respect to presentation of the target is resulted from a fact that the examinee can perceive the target based on a detection result of the brain activity detecting unit and which obtains the visual field condition of the examinee's eye based on the presentation condition of the target and the response result with the response unit in consideration of the determination result.

(2) The perimeter according to (1), wherein the operation unit does not adopt the response with the response unit when the operation unit determines that the response with the response unit with respect to the presentation of the target is not resulted from the fact that the examinee can perceive the target.

(3) The perimeter according to (2), further comprising a control unit which controls the target presenting unit so as to present the target again when the operation unit does not adopt the response with the response unit under the same presentation condition as the case that the response with the response unit is not adopted.

(4) The perimeter according to (1), wherein
the brain activity detecting unit comprises an irradiating unit which irradiates near infrared light to the visual cortex and a photo-detecting unit which detects the light passing and scattering through the visual cortex, and detects the activity condition of the visual cortex based on a detection result of the photo-detecting unit when the target is presented and the detection result of the photo-detecting unit when the target is not presented.

(5) The perimeter according to (4),
wherein the irradiating unit irradiates first near infrared light in which an absorbance coefficient of oxygenated hemoglobin is higher than that of deoxygenated hemoglobin and second near infrared light in which the absorbance coefficient of the oxygenated hemoglobin is lower than that of the deoxygenated hemoglobin to the visual cortex;
the photo-detecting unit detects the first and second near infrared light passing and scattering through the visual cortex; and
the brain activity detecting unit detects the activity condition of the visual cortex based on comparison between respective detected light amounts of the first and second near infrared light when the target is presented and respective detected light amounts of the first and second near infrared light when the target is not presented.

DETAILED DESCRIPTION OF PREFERRED EMBODIMENTS

Figure 1:
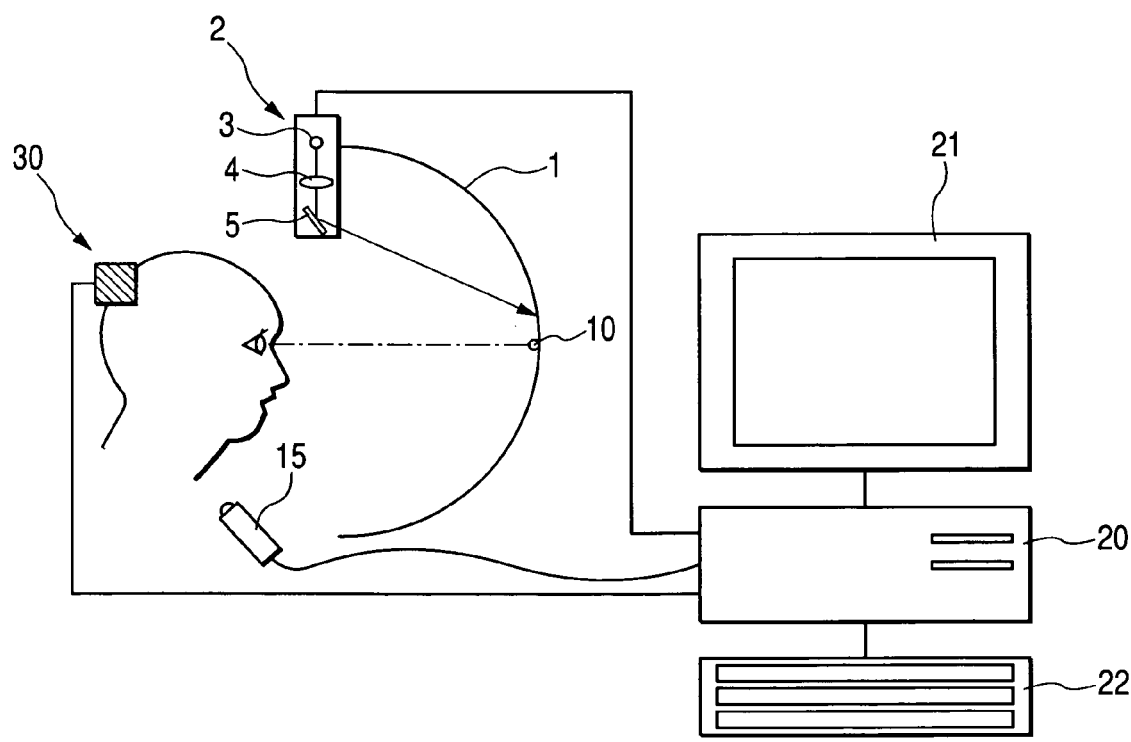
FIG. 1 is a schematic block diagram of a perimeter according to an embodiment of the present invention.

Hereinafter, an embodiment according to the present invention will be described with reference to the drawings. FIG. 1 is a schematic block diagram of a perimeter according to the embodiment of the present invention.

A semi-sphere dome-type screen 1 is arranged in front of an examinee's eye and a stimulation target for examination is projected on the screen 1 by a target projecting unit 2. The target projecting unit 2 includes a light source 3, a projection lens 4, and a movable mirror 5. The movable mirror 5 is driven by a driving mechanism (not illustrated) to change a position of the spot-type stimulation target to be projected on the screen 1 by the light source 3 and the projection lens 4. The movable mirror 5 can be constituted by two sets of galvanic mirrors. A fixation target 10 is provided at a center of the screen 1. The target projecting unit 2 is connected to an operation controlling unit 20. The operation controlling unit 20 drives and controls the movable mirror 5 to change the position of the stimulation target to be projected on the screen 1. The operation controlling unit 20 changes brightness (luminance) of the stimulation target to be projected on the screen 1 by adjusting the light amount of the light source 3. A monitor 21, an input device 22 such as a keyboard, a response button 15 and the like are connected to the operation controlling unit 20.

Figure 2:
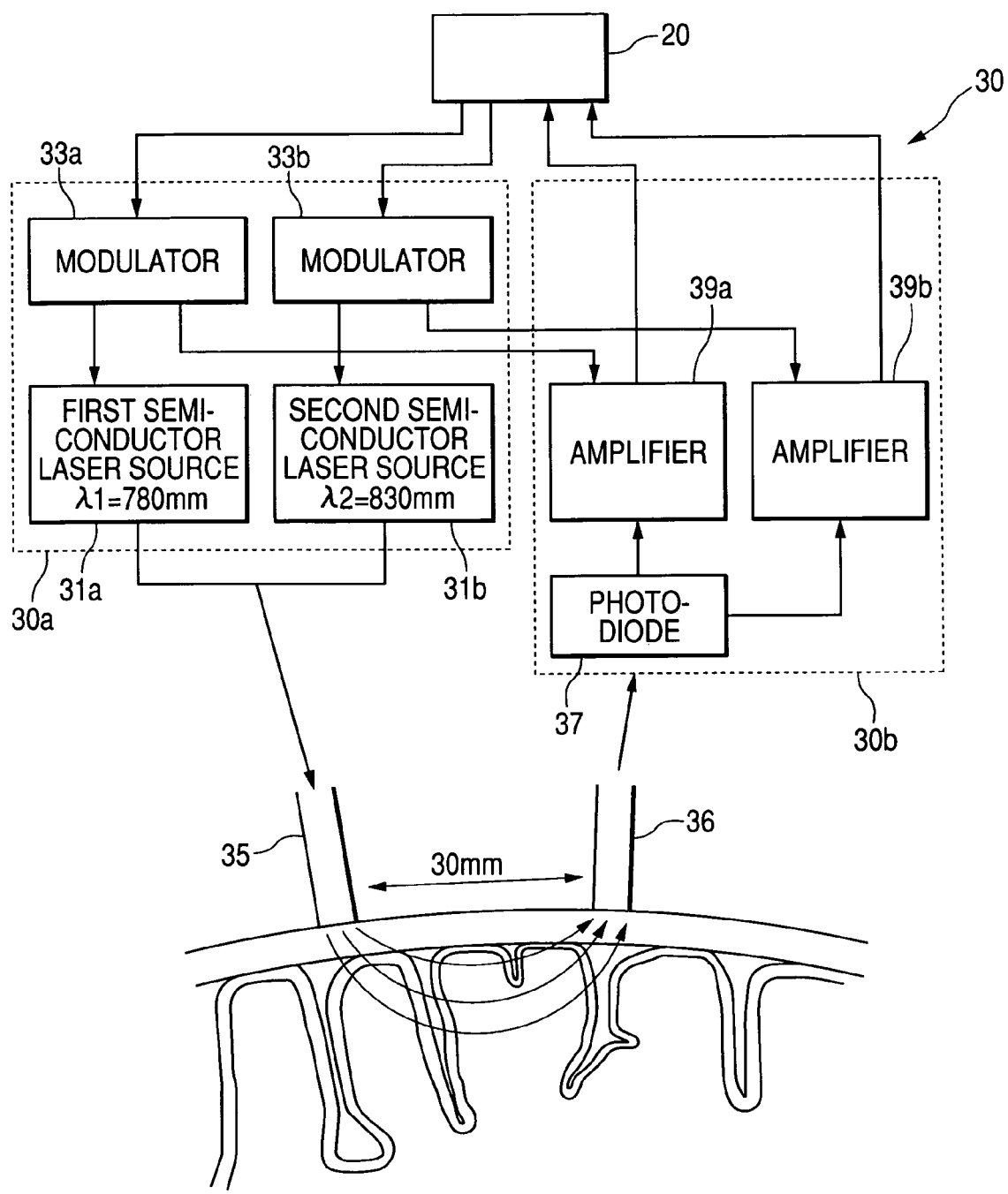
FIG. 2 is a schematic block diagram of a probe for detecting a brain activity that is attached to an occipital area of an examinee.

The schematic constitution of a probe 30 for detecting a brain activity to be attached to an occipital area of the examinee will be described with reference to FIG. 2. The probe 30 includes an irradiating unit 30a which irradiates near infrared light to the occipital area and a photo-detecting unit 30b which detects the light passing and scattering through the a visual cortex (a visual area of a cerebral cortex) in the occipital are. The irradiating unit 30a includes a first semiconductor laser source 31a for emitting near infrared light of a wavelength λ1=780 mm, a second semiconductor laser source 31b for emitting near infrared light of a wavelength λ2=830 mm, a modulator 33a connected to the laser source 31a, a modulator 33b connected to the laser source 31b, and an optical fiber 35 for irradiating the near infrared light emitted from the laser sources 31a and 31b to the occipital area. The photo-detecting unit 30b includes an optical fiber 36 for detection that is arranged separated from the front end of the optical fiber 35 at an interval about 30 mm on the occipital area, an avalanche photodiode 37 that is a photo-detector for detecting the light input in the optical fiber 36, and lock-in amplifiers 39a and 39b for referring to modulated frequencies of the modulators 33a and 33b. The probe 30 is connected to the operation controlling unit 20, respective laser sources 31a and 31b are driven and controlled, and an electric signal corresponding to light strength of each light detected by the photodiode 37 is output. As this probe 30, one used for optical topography can be basically used, however, at least one set of the irradiating unit 30a and the photo-detecting unit 30b may be available because the present apparatus does not intend to acquire a map of the brain activity but it may detect the activity condition of the visual cortex.

A measurement principle for measuring the activity condition of the visual cortex by using the probe 30 is based on a near infrared light spectroscopic method. The near infrared light spectroscopic method will be described below.

Generally, light is recognized not to pass through a living body. However, light of a near infrared range (700 to 1300 nm), a so called "optical window", passes through the living body relatively well because the light of the near infrared range is less influenced by scattering than light of a visible range and is less absorbed by water than light of an infrared range. Therefore, irradiating the light of 800 nm on a palm and picking up the transparent image thereof by a CCD camera, the image reflects hemoglobin of a blood flowing through blood vessel differently from an X-ray image describing absorption of a bone.

Figure 3:
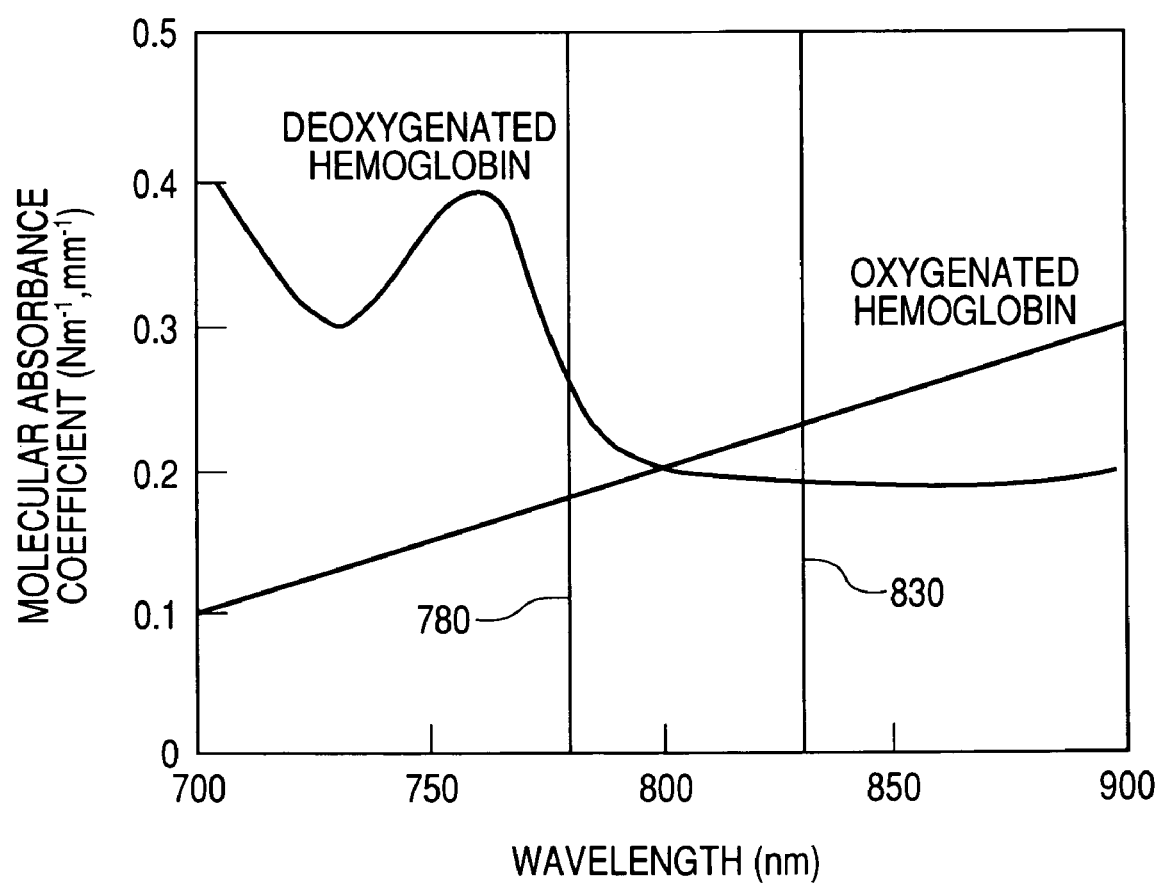
FIG. 3 is a view showing an absorbance spectrum indicating an absorbance (represented by a vertical axis) with respect to a wavelength (a horizontal axis).

On the other hand, hemoglobin in blood to carry oxygen changes its color (spectrum) when it is connected to oxygen (oxygenated hemoglobin) and when it is separated from oxygen (deoxygenated hemoglobin). FIG. 3 shows an absorbance spectrum indicating an absorbance (a vertical axis) with respect to a wavelength (a horizontal axis). As being obvious from this drawing, in the near infrared range, the oxygenated hemoglobin and the deoxygenated hemoglobin have characteristic absorbance property such that their absorbance are equal in the vicinity of 800 nm and the absorbance inverts at the opposite sides. In other words, in the wavelength band longer than 800 nm, the absorbance of the oxygenated hemoglobin is made higher, and in the wavelength band shorter than 800 nm, the absorbance of the deoxygenated hemoglobin is made higher. Accordingly, in the visible range where human can perceive (visually recognize), the oxygenated hemoglobin can be seen in vivid red and the deoxygenated hemoglobin can be seen in dark red, however, in the longer wavelength range, they are inverted. The biospectrometry with near infrared light serves to measure oxygen density within the living body by using a difference between two types of the hemoglobin as described above. In other words, with utilizing the properties of the hemoglobin, it is possible to continuously measure oxygen condition of the inside of the living body by checking the light passing through the inside of the diving body using this hemoglobin property, without withdrawing blood (without observing blood) and without injuring a body (without invading a body).

According to an actual apparatus, the measurement is carried out by combining an irradiating unit which irradiates near infrared light to the living body and a photo-detecting unit which receives and detects the light passing and scattering through the inside of the living body. According to the present apparatus, as shown in FIG. 2, irradiating the near infrared light of 780 nm from the laser source 31a and the near infrared light of 830 nm from the laser source 31b to the occipital area through the optical fiber 35, the photodiode 37 connected to the occipital area through the optical fiber 36 detects the light when the light is released from the occipital area after scattering and passing through the visual cortex in the occipital area. The light released from the occipital area includes the hemoglobin absorption information within the visual cortex. By obtaining this information, it is possible to measure the change of oxygenation in the visual cortex.

More specifically, near infrared light A of a wavelength (longer than 800 nm) in which an absorbance coefficient of the oxygenated hemoglobin (Oxy-Hb) is higher than that of the deoxygenated hemoglobin (Deoxy-Hb) and near infrared light B of a wavelength (shorter than 800 nm) in which an absorbance coefficient of the oxygenated hemoglobin (Oxy-Hb) is lower than that of the deoxygenated hemoglobin (Deoxy-Hb) are irradiated to the occipital area, and the light is received by the photo-detector through the optical fiber for detection that is separated from there about 30 nm.

In near infrared light, the absorbance coefficient $\mu a = \epsilon C$ depends on two variables of a molecular absorbance coefficient $\epsilon$ and density $C$. Then, in order to obtain the density $C$ from the absorbance coefficient $\mu a$, $\epsilon$ that is a value of the optical absorbance spectrum is required in advance. If respective absorbance coefficients $\mu a1$ and $\mu a2$ are derived by measuring the change of oxygenation by using two wavelengths representing a characteristic of a spectrum is measured, the following simultaneous equations are established from a relationship equation of $\mu a = \epsilon C$.

$$\lambda a1 = \epsilon(Oxy\lambda 1) \cdot C(Oxy\text{-}Hb) + \epsilon(Deoxy\lambda 1) \cdot C(Deoxy\text{-}Hb)$$

$$\lambda a2 = \epsilon(Oxy\lambda 2) \cdot C(Oxy\text{-}Hb) + \epsilon(Deoxy\lambda 2) \cdot C(Deoxy\text{-}Hb)$$

Solving this equation, it is possible to derive the density C of the oxygenated hemoglobin, namely, C(Oxy-Hb) and the density C of the deoxygenated hemoglobin namely, C(Deoxy-Hb). The, sum C(Oxy-Hb)+C(Deoxy-Hb) means the blood amount and the ratio C(Oxy-Hb)/C(Oxy-Hb)+C(Deoxy-Hb) means oxygen saturation. In other words, if the absorbance coefficient of the light is obtained, the blood amount and the oxygen saturation can be also obtained.

Normally, the brain activity consumes oxygen in accordance with a nervous activity, so that the blood amount to the activated region is increased in order to provide oxygen thereto and further, the oxygenated hemoglobin is increased and deoxygenated hemoglobin is decreased. Thus, in the near infrared light A, the absorption light amount is increased and the detected light amount is decreased in accordance with increase of the oxygenated hemoglobin. On the other hand, in the near infrared light B, the absorption light amount is decreased and the detected light amount is increased in accordance with decrease of the deoxygenated hemoglobin. However, since the blood amount is increased, decrease of the deoxygenated hemoglobin is not so much as increase of the oxygenated hemoglobin, and increase of the detected light amount of the near infrared light B is smaller than decrease of the detected light amount of the near infrared light A.

Accordingly, if the visual stimulation is given to the examinee in practice, it results in that the density C(Oxy-Hb) of the oxygenated hemoglobin is increased and the density C(Deoxy-Hb) of the deoxygenated hemoglobin is decreased, the blood amount C(Oxy-Hb)+C(Deoxy-Hb) is increased, and the oxygen saturation C(Oxy-Hb)/C(Oxy-Hb)+C(Deoxy-Hb) is increased. Using a parameter that is changed the most among these changes to the visual stimulation as an index, it is possible to detect the activity condition of the visual cortex with a high degree of accuracy. In addition, combinations of some changes may be available to detect the activity condition.

Next, the examination of the state of the visual field will be described below. The optical fibers 35 and 36 of the probe 30 are arranged on the occipital area. The operation controlling unit 20 modulates the near infrared light emitted from the laser sources 31a and 31b through the modulators 33a and 33b. The near infrared light of two wavelengths emitted from the laser sources 31a and 31b are mixed and irradiated from the optical fiber 35. The light released after scattering and passing through the visual cortex in the occipital area is received by the photodiode 37 through the optical fiber 36. Signals output from the photodiode 37 are demodulated by the amplifiers 39a and 39b, and then, the detection of two wavelengths is distinguished. The signals output from the amplifiers 39a and 39b are input in the operation controlling unit 20. The operation controlling unit 20 calculates the density C (Oxy-Hb) of the oxygenated hemoglobin, the density C(Deoxy-Hb) of the deoxygenated hemoglobin, the blood amount C(Oxy-Hb)+C(Deoxy-Hb), and the oxygen saturation C(Oxy-Hb)/C(Oxy-Hb)+C(Deoxy-Hb), and monitors the brain activity. Respective values are measured in a state that the examinee fixes the examinee's eye on the fixation target 10, and are stored in a memory of the operation controlling unit 20.

Next, the operation controlling unit 20 controls the target projecting unit 2 to project the stimulation target on the screen 1, the target is presented to the examinee. Then, the examiner makes the examinee to respond with the response button 15 when the examinee can perceive the presented target in the state that the examinee fixes the examinee's eye on the fixation target 10 at the center of the screen 1. When the response with the response button 15 is found, the respective values are measured and the change of them is detected. Generally, if the examinee can perceive the target and the examinee's visual cortex reacts, the consumption of oxygen is increased at this portion, thereby the density C(Oxy-Hb) of the oxygenated hemoglobin, the blood amount C(Oxy-Hb)+C(Deoxy-Hb), and the oxygen saturation C(Oxy-Hb)/C(Oxy-Hb)+C(Deoxy-Hb) are increased and the density C (Deoxy-Hb) of the deoxygenated hemoglobin is decreased. If the examinee responds with the response button 15 although the examinee cannot perceive the target, the respective values are not changed, so that it is possible to determine that the examinee responds by mistake.

The operation controlling unit 20 randomly changes the presentation position of the target in accordance with a program for examination. Further, the operation controlling unit 20 changes the presentation brightness of the target at each presentation position into dark brightness gradually and measures a threshold value that the examinee can perceive. The operation controlling unit 20 adopts the response when it determines that the examinee can perceive the target and responds with the button 15 by referring the detection of the activity condition of the visual cortex by the probe 30. On the other hand, when the operation controlling unit 20 determines that the examinee cannot perceive the target but responds, it may not adopt the response. In this case, the operation controlling unit 20 controls the target presenting unit 2 so as to present the target again under the same presentation condition and repeats the examination (the order of repeating the examination is randomly decided after presenting the target on other presentation position). Thereby, the examination of the visual field with a high degree of precision is possible, which does not only depend on the consciousness of the examinee. Further, reliability of the examination result may be calculated on the basis of the result that the examinee responds by error by referring detection of the activity condition of the visual cortex by the probe 30, the reliability may be displayed on the monitor 21. In other words, if the examinee responds by error in many times, the reliability of the examination result is made low, and if the examinee responds by error in few times, the reliability of the examination result is made high.

Incidentally, the above-described embodiment is described taking a static perimeter as an example. However, the present invention can be also applied to a dynamic perimeter for moving the stimulation target of predetermined brightness and making the examinee to respond with respect to a point of time when the examinee cannot perceive the target. Further, the perimeter is not limited to a type presenting the target on the dome-type screen but it may be a type presenting the target on an electronic display unit such as a liquid crystal display. Further, the perimeter according to the present invention can be applied to a scotometry that is carried out by directly projecting the stimulation target on a retina by a SLO (scanning Laser Ophthalmoscope), visumetry, microperimetry and the like.

What is claimed is:

1. A perimeter for examining visual field condition of an examinee's eye, the perimeter comprising:

a target presenting unit which presents a stimulation target for examination to the examinee's eye, a presentation condition of the target including a presentation position of the target being variable;

a response unit with which the examinee responds when the examinee can perceive the presented target;

a brain activity detecting unit which detects activity condition of a visual cortex of the examinee; and an operation unit which determines whether or not the response with the response unit with respect to presentation of the target is resulted from a fact that the examinee can perceive the target based on a detection result of the brain activity detecting unit and which obtains the visual field condition of the examinee's eye based on the presentation condition of the target and the response result with the response unit in consideration of the determination result.

2. The perimeter according to claim 1, wherein the operation unit does not adopt the response with the response unit when the operation unit determines that the response with the response unit with respect to the presentation of the target is not resulted from the fact that the examinee can perceive the target.

3. The perimeter according to claim 2, further comprising a control unit which controls the target presenting unit so as to present the target again when the operation unit does not adopt the response with the response unit under the same presentation condition as the case that the response with the response unit is not adopted.

4. The perimeter according to claim 1, wherein
the brain activity detecting unit comprises an irradiating unit which irradiates near infrared light to the visual cortex and a photo-detecting unit which detects the light passing and scattering through the visual cortex, and detects the activity condition of the visual cortex based on a detection result of the photo-detecting unit when the target is presented and the detection result of the photo-detecting unit when the target is not presented.

5. The perimeter according to claim 4,
wherein the irradiating unit irradiates first near infrared light in which an absorbance coefficient of oxygenated hemoglobin is higher than that of deoxygenated hemoglobin and second near infrared light in which the absorbance coefficient of the oxygenated hemoglobin is lower than that of the deoxygenated hemoglobin to the visual cortex;
the photo-detecting unit detects the first and second near infrared light passing and scattering through the visual cortex; and
the brain activity detecting unit detects the activity condition of the visual cortex based on comparison between respective detected light amounts of the first and second near infrared light when the target is presented and respective detected light amounts of the first and second near infrared light when the target is not presented.

* * * * *